(12) United States Patent
Moskowitz et al.

(10) Patent No.: US 9,144,363 B2
(45) Date of Patent: Sep. 29, 2015

(54) EXTRACTION AND ABSORBENT PAD (75) Inventors: Darryl Moskowitz, Buffalo Grove, IL (US); Michael Grills, Chicago, IL (US)

(73) Assignees: Darryl Moskowitz, Buffalo Grove, IL (US); Michael Grills, Buffalo Grove, IL (US)

( * ) Notice: Subject to any disclaimer, the term of this patent is extended or adjusted under 35 U.S.C. 154(b) by 599 days.

(21) Appl. No.: 13/476,360

(22) Filed: Jun. 14, 2012

(65) Prior Publication Data
US 2013/0333724 A1    Dec. 19, 2013

(51) Int. Cl.
*A47L 13/16* (2006.01)
*A61F 13/15* (2006.01)

(52) U.S. Cl.
CPC *A47L 13/16* (2013.01); *A61F 13/15* (2013.01)

(58) Field of Classification Search
CPC .................................. A47L 13/16; A61F 13/15
USPC .............................. 15/208, 209.1, 210.1, 215
See application file for complete search history.

(56) References Cited

U.S. PATENT DOCUMENTS

| | | | | |
|---|---|---|---|---|
| 6,048,123 | A * | 4/2000 | Holt et al. | 401/138 |
| 7,102,054 | B1 * | 9/2006 | Cree et al. | 604/378 |
| 7,144,173 | B2 * | 12/2006 | Policicchio et al. | 401/138 |
| 2003/0028985 | A1 * | 2/2003 | Prodoehl et al. | 15/118 |
| 2005/0268419 | A1 * | 12/2005 | Tanaka | 15/209.1 |
| 2007/0107151 | A1 * | 5/2007 | Pung et al. | 15/104.94 |
| 2010/0058551 | A1 * | 3/2010 | McDowell | 15/210.1 |

* cited by examiner

*Primary Examiner* — Randall Chin
(74) *Attorney, Agent, or Firm* — Emch, Schaffer, Schaub & Porcello, Co. L.P.A.

(57) ABSTRACT

An extraction or absorbent pad that can be used to pick up spills and/or to remove spots from a surface. The absorbent pad has a core made of a super absorbent polymer laminate, a fluid impervious sheet positioned on one side of the core and a non-woven sheet positioned on the opposite side of the core from the fluid impervious sheet. A handle is provided on the pad to assist with transporting the pad without touching the portion of the pad that absorbs fluids.

22 Claims, 6 Drawing Sheets

EXTRACTION AND ABSORBENT PAD

BACKGROUND OF THE INVENTION

There is a need for an extraction or absorbent pad that can effectively absorb and remove spills and stains. Most spills and stains are managed by placing a cotton towel or paper towels on the spill or stain. The cotton and paper towels are only somewhat effective in absorbing the spills and stains. These products do not have any significant ability to retain the spill and frequently the spill leaks from the towel and creates additional removal issues. The paper or cotton towels are not the proper tool for the job. These towels only remove the fluid on the surface and do not extract the portion of the fluid that has moved below the surface. Accordingly, there is a need for a product that can absorb and retain spills and stains. It is also desirable for the product to be able to wick spills and stains from the surface and the interior of a material such as carpet.

SUMMARY OF THE INVENTION

The present invention is directed to an extraction or absorbent pad that can be used to pick up spills or to remove spots from a surface. The absorbent pad has a core made of a super absorbent polymer laminate, a fluid impervious sheet positioned on one side of the core and a non-woven sheet positioned on the opposite side of the core from the fluid impervious sheet. A handle is provided on the pad to assist with transporting the pad without touching the portion of the pad that absorbs fluids.

Other objects and advantages of the present invention will become apparent to those skilled in the art upon a review of the following detailed description of the preferred embodiments and the accompanying drawings.

DETAILED DESCRIPTION OF THE PREFERRED EMBODIMENT(S)

The invention is related to an extraction or absorbent pad that can be used to pick up spills or to remove spots from a surface. The absorbent pad has a core made of a super absorbent polymer laminate, a fluid impervious sheet positioned on one side of the core and a non-woven sheet positioned on the opposite side of the core from the fluid impervious sheet. A handle is provided on the pad to assist with transporting the pad without touching the portion of the pad that absorbs fluids. The features of the invention will be more readily understood by referring to the attached drawings in connection with the following description.

As shown in FIGS. 1-5 the absorbent pad 10 has a core 15 that is formed of a super absorbent polymer laminate. The super absorbent polymer laminate has a plurality of super absorbent particles 17 positioned between two tissue layers 19. The tissue layers 19 function to hold the super absorbent particles 17 in a spaced apart desired orientation. Additional materials such as cotton fluff can also be positioned around the super absorbent particle 17 to provide additional absorbent characteristics for the core 15. The super absorbent particles 17 have a large surface area that functions to draw fluids into the particles where the fluid is retained. The super absorbent particles 17 are capable of absorbing many times there own weight in fluid. A particularly good example of a super absorbent polymer product that can be used in the core 15 is Gelok which is available from Gelok International.

It is well known that a sphere has the highest volume-to-surface area of any three dimensional shape, described by the formula $V=4/3\pi r^3$. It is also well known that as the diameter (size) of a sphere decreases, the area of the surface becomes greater per unit volume. The shape of the super absorbent polymer particles, although imperfect, are generally regarded as spherical in shape. The rate at which these polymer particles absorb water is directly related to their surface area (smaller particles=more surface area=faster uptake), while overall capacity is directly related to the volume of the polymer particle (larger particles=more volume=higher capacity). Therefore the uptake rate (speed) and overall volume (capacity) can be tailored to a given application by selecting polymer particles of a size or combination of sizes to achieve the desired results.

Examples would include:

An animal accident requires a quick uptake so that the offending liquid doesn't have time to work its way deep into the carpet fibers, or the carpet padding, where it is difficult to remove by any process. Capacity is not the issue here.

With a spilled pitcher of water, the fluid is benign, but voluminous. Having the capacity to remove the entire half gallon in one application is more important than getting a quart of it up quickly and having to repeat the process with a second pad.

Physical dimensions, design capacity and uptake rate are determined by the intended use for the pad. But retail packaging and/or pads per package considerations can also come into play. Therefore mixing particle sizes and the quantity of the polymer particles to give the desired result for the application, within the physical constraints of the pad and packaging is desirable. In practice it has been found desirable to have the particles of super absorbent polymer be in the range from about 100 microns to about 900 microns, with particles from about 140 microns to about 500 microns being preferred.

Figure 1:
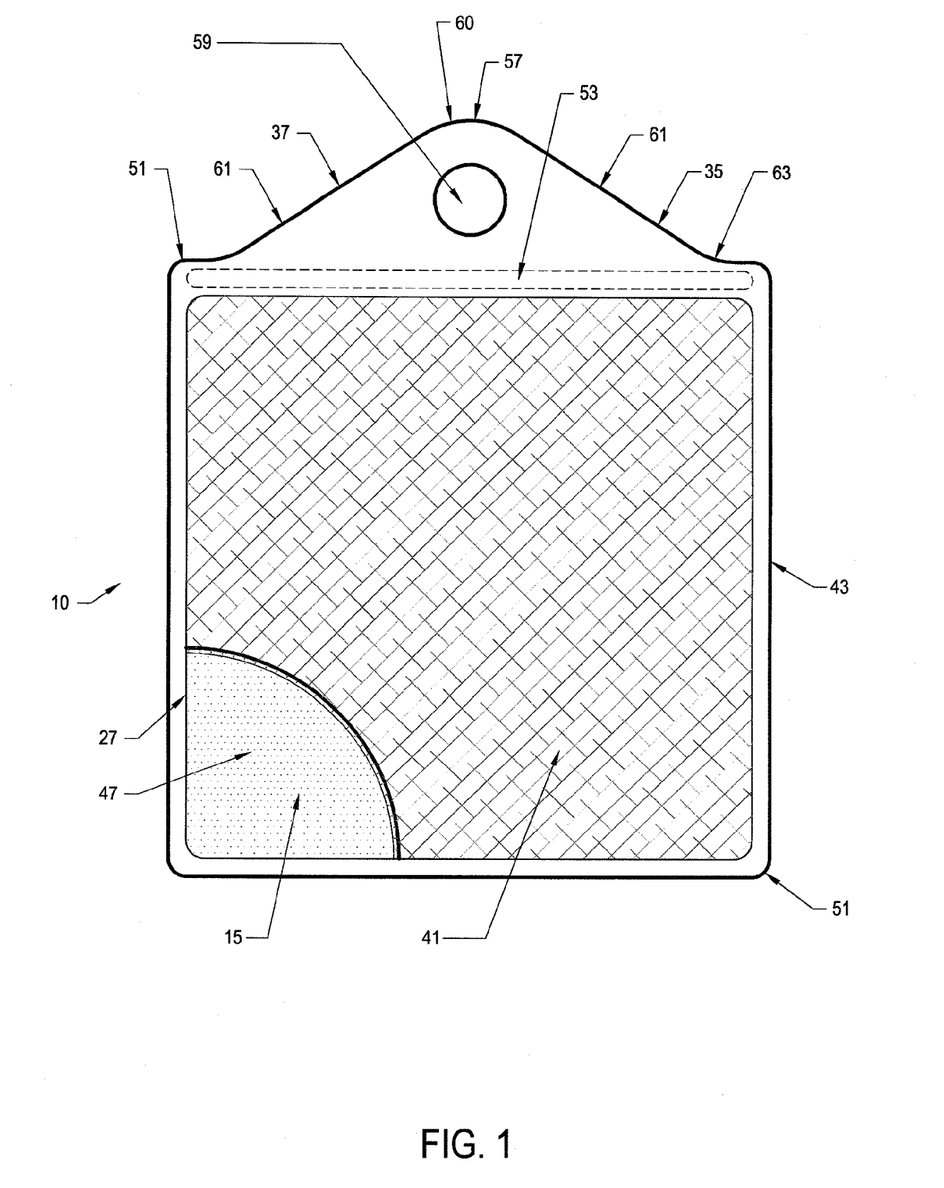
FIG. 1 is a front elevational view of the absorbent pad of the present invention.
Figure 2A:
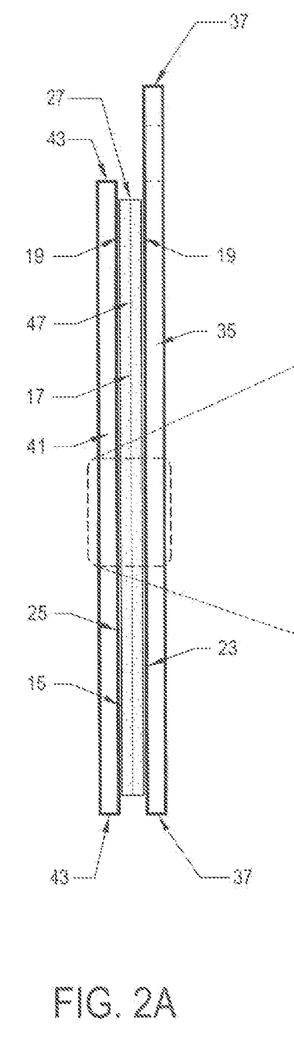
FIG. 2A is a side elevational cross sectional view and FIG. 2B is an enclosed portion of the cross sectional view shown in FIG. 2A.
Figure 2B:
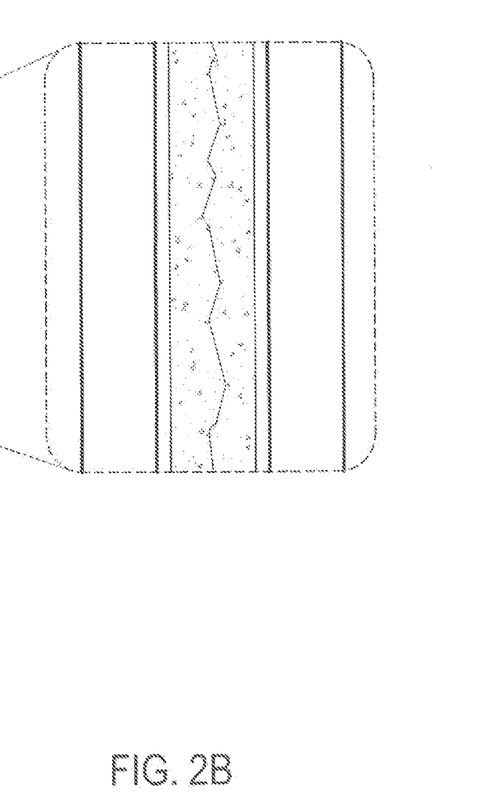

The core 15 has a first surface 23 and a second surface 25. The core 15 defines an outer perimeter 27 that defines the outer boundary of the core 15.

A fluid impervious sheet 35 is positioned adjacent the first surface 23 of the core 15. The fluid impervious sheet has an outer peripheral edge 37 that extends beyond the outer perimeter 27 of the core 15. The fluid impervious sheet is usually formed of a hydrophobic material that resists fluid and is generally impervious to the flow of fluids. Polyethylene films having a thickness from about 0.5 mils to about 5 mils have been found to be particularly useful for the fluid impervious sheet 35. A polyethylene film designated EX 487 manufactured by Tredegar and having a thickness of approximately 3.0 mils has been found to work particularly well for the fluid impervious sheet 35. The fluid impervious sheet 35 is usually made of a translucent material.

A non-woven sheet 41 is positioned adjacent the second surface 25 of the core 15. The non-woven sheet 41 generally has a thickness from about 2 mils to about 30 mils and a basis weight from about 25 gsm to about 175 gsm. In practice it has been found that a non-woven sheet having a thickness of about 8 mils to about 15 mils and a basis weight of about 50 gsm to about 140 gsm works particularly well for the sheet 41. The non-woven is designed to wick fluids through the non-woven sheet and the non-woven material is usually a hydrophilic material to assist in this wicking action. It has been found that the non-woven sheet can be made of Sontara No. 8801 which is a non-woven product made by Dupont. The non-woven sheet has an outer peripheral boundary 43 that extends beyond the outer perimeter 27 of the core 15. The outer peripheral boundary 43 of the non-woven sheet 41 is bonded to the outer peripheral edge 37 of the fluid impervious sheet 35 to form an enclosed space 47. The core 15 is positioned so that it is within the enclosed space 47 defined by the fluid impervious sheet 35 and the non-woven sheet 41. The enclosed space 47 can expand outwardly, in a direction perpendicular to the surface of the core 15, as the core 15 absorbs and retains fluids. This expansion capability allows the pad 10 to effectively handle large spills and to absorb and retain the spilled fluid in the core of the pad. The enclosed space 47 is designed to expand to allow the particles to absorb and retain the maximum quantity of fluid.

A pad 10 without a core, like a pillowcase without a pillow, has an internal volume approaching zero. As the pad will contain a number of super absorbent polymer particles—which, when exposed to any of a variety of liquids, expand to many times their original size—it is critical to know the maximum capacity (volume) of a distended pad, so that a product failure (rupture) will not occur.

Super absorbent polymer particles are measured in microns. Though too small to count, it is still necessary to know the volume that each one will occupy when fully saturated under ideal conditions. This information can often be derived from manufacturer data sheets or measured empirically.

A pad for the home might need to meet existing dimensional criteria, such as the width of a roll of paper towels. The amount of polymer would be tailored to the shape. Conversely, a pad could be designed to absorb a spill of a known quantity, such as a cup of water. In this case, the shape would be selected to match the polymer capacity. In either case, it might be necessary to blend various polymers together, in order to tailor the speed of uptake and the overall absorptive capacity for the application. While it has been explained that pad capacity, must not be less than the volume of the swollen polymers within, it is equally important to keep cost and waste to a minimum, calling for the smallest pad for the intended purpose.

Therefore, a formula that can evaluate combinations of polymers, and calculate the maximum amounts of each polymer for a given pad size, or calculate the size of the pad based upon the required polymer mix for a given application is useful.

After entering the variables in the following equation, if the left side (before the ≥ sign) is equal to the right side, the pad capacity, and that of the saturated polymers are equivalent and therefore ideal. If the left side of the equation is less than the right side, then product failure (rupture) is possible.

If the left side of the equation is more than the right side, then there is wasted material (the pad is larger than necessary) and therefore less profit is realized.

$$\text{Sqrt}(w*l/3)^3 \geq \text{Sum}(n_k * \pi * d_k^3/6)$$

$$k=1 \ldots q$$

w is the width of the pad in millimeters.

l is the length of the pad in millimeters.

n is the number of polymer particles (for each type $n_1 \ldots n_q$).

d is the average diameter of a fully saturated particle ($n_1 \ldots n_q$) in millimeters. Each type of polymer (if more than one is used) is likely to have its own diameter.

Polymer particles are imperfect spheres wet or dry, but are especially conformable when wet, forming a homogenous gelatinous material. This characteristic makes it unnecessary to calculate for the spaces between fully saturated polymer particles, as you would for solid non-conformable particle spheres.

Certain post-calculation conversions may be required, such as converting liters to gallons or particles to grams. A characteristic of dense polymer packing referred to as 'gel blocking', which reduces the total capacity and speed of uptake, can occur in some designs. Though costs increase accordingly, gel blocking can be minimized by numerically increasing the left side of the equation in relation to the right side, effectively putting more polymer adjacent to the contact surface.

The variables in this formula, when input into a computerized spreadsheet program, may be changed and tested to optimize polymer combinations and pad size.

All units in the formula are metric and the formula is for rectangular pads.

The non-woven material is designed to wick fluid into the enclosed space 47 where the core 15 is positioned. It has been found that hydrophilic non-woven material works very well to wick fluid to the core 15 in the enclosed space 47. The super absorbent polymer 17 that is present in the core 15 absorbs and retains any fluids that are wicked into the core by the non-woven sheet 41. Accordingly, the absorbent pad 10 is designed to draw fluids through the non-woven sheet 41 into the core 15 where the super absorbent polymer particles will absorb and retain the fluids. The high percentage of super absorbent polymer in the core is very effective at reducing or controlling odors that may be present in the fluids that are absorbed and retained in the core. It is also possible that an odor control substance can be incorporated into the material of the core 15 to provide additional odor control. The absorption qualities of the super absorbent polymer allow the absorbent pad to be relatively thin, but at the same time absorb and retain a significant quantity of fluids.

The translucent characteristic that is usually present in the fluid impervious sheet 35 allows the user of the absorbent pad 10 to determine if the core 15 has absorbed and retained fluids, but not to directly visualize the fluids that have been absorbed and retained.

In most applications, the absorbent pad 10 will be a simple polygon such as a generally square shape for vertical spills where a round shape would more closely match the spill, but a round shape would increase manufacturing waste and is not a practical shape for embedding a handle. A generally rectangular shape for the pad is preferred where the spilled liquid had a sideways component of inertia and produced a pattern that is longer than it is wide. One skilled in the art would recognize that other shapes are also possible. The corners 51 formed at the edges of such a square or rectangular shaped product are rounded and have a radius from about ⅛ to about 1 inch. The radius shape of the corners 51 allow the corners to distribute loads more effectively and reduce the potential of the corners to function as a potential failure point in the bonding between the non-woven sheet 41 and the fluid impervious sheet 35. As the super absorbent polymer particles 17 of the core 15 are capable of absorbing and retaining many times their weight in fluids a significant quantity of fluid can be absorbed and retained in the core 15. The weight of the fluid and the hydraulic forces that are generated on the pad when force is applied to the pad can create significant loads that stress the structure of the pad. The rounded corners 51 allow this significant quantity of absorbed and retained fluid to be maintained in the core 15 in the enclosed spaced 47 and the rounded shape of the corners 51 enhances the strength of the corners to prevent failures in this region of the absorbent pad 10.

Figure 6:
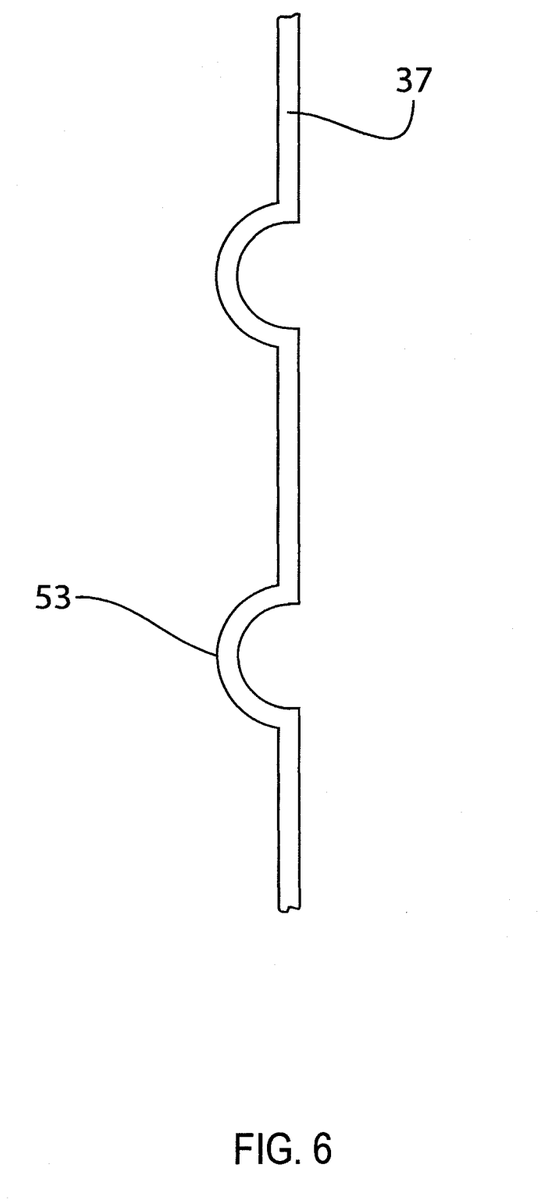
FIG. 6 is a partial side elevational view of a portion of the fluid impervious sheet used in the pad.

In many applications it has been found desirable to include a handle 57 on the absorbent pad 10 to assist in positioning the pad in an area to absorb fluids and for removing the pad once the fluids have been absorbed and retained in the core 15. In practice it has been found desirable to form the handle 57 as part of the fluid impervious sheet 35 that is positioned adjacent the first surface 23 of the core 15. The fluid impervious sheet 35 can be designed to extend beyond the outer peripheral boundary 43 of the non-woven sheet 41 on one side of the absorbent pad 10 to form the handle. It has been found desirable to have the handle 57 extend across substantially the entire side of the absorbent pad 10 so that the handle will have sufficient strength capable of lifting the absorbent pad once the absorbent pad has absorbed and retained fluids. In practice it has been found that the handle should be more than ½ of the width of the edge of the pad and preferably extends from about 60% to about 100% of the length of one edge of the absorbent pad 10. The width of the handle 57 also assists in preventing the pad from twisting or folding when the pad is positioned or removed by the handle 57. In some applications a stiffening rib 53 can be positioned in the region of the handle to further reduce twisting of the pad 10. The rib can be a rod added between the fluid impervious sheet 35 and the non-woven sheet 41 or the rib can be embossed or formed into the fluid impervious sheet. As shown in FIG. 6, more than one rib 53 can be used and the ribs can be positioned along the fluid impervious sheet in areas other than the handle. The realities of manufacturing and economics dictate that the pad be made from materials that get the job done, while keeping costs to a minimum. Like a plastic shopping bag, it must be strong enough for its intended purpose, but inexpensive enough that it makes commercial sense. But unlike a plastic shopping bag, the pad of the present invention may contain offensive fluids. Therefore, leaks are undesirable, but fluid control is always a difficult proposition. To that end we have integrated a handle into the pad itself, rather than attaching something to it that could tear off, resulting in the pad striking the floor and possibly rupturing. The handle was designed to run the majority of the length of one of the sides of the pad to help reduce, and more uniformly spread, the stress across the material to help prevent tearing. In some applications it has been found desirable to have aperture 59 formed in the handle 57 to provide an additional gripping area that can be utilized when using the handle 57 to move the pad. In most applications the aperture will have a diameter from about 0.5 to about 2 inches to allow a finger or multiple fingers of a user be positioned in the aperture while positioning or removing the absorbent pad 10. The handle 57 can have a generally triangular shape where the peak 60 of the triangle is spaced apart from the core 15. The legs 61 of the triangular shaped handle join with the portion of the fluid impervious sheet 35 that extends beyond the non-woven sheet 41. The peak is usually positioned to be in the center of the side of the pad 10 upon which the handle is positioned. The peak usually has a rounded configuration to be more user friendly when used. The peak usually has a radius of curvature from about 0.5 to about 6 inches. The legs 61 have a rounded shape 63 where the legs join the portion of the fluid impervious sheet 35 that extends beyond the non-woven sheet 41. The rounded shape 63 is formed by a radius of curvature from about 0.5 to about 2 inches where the legs join the portion of the fluid impervious sheet that extends beyond the non-woven sheet 41.

Figure 4:
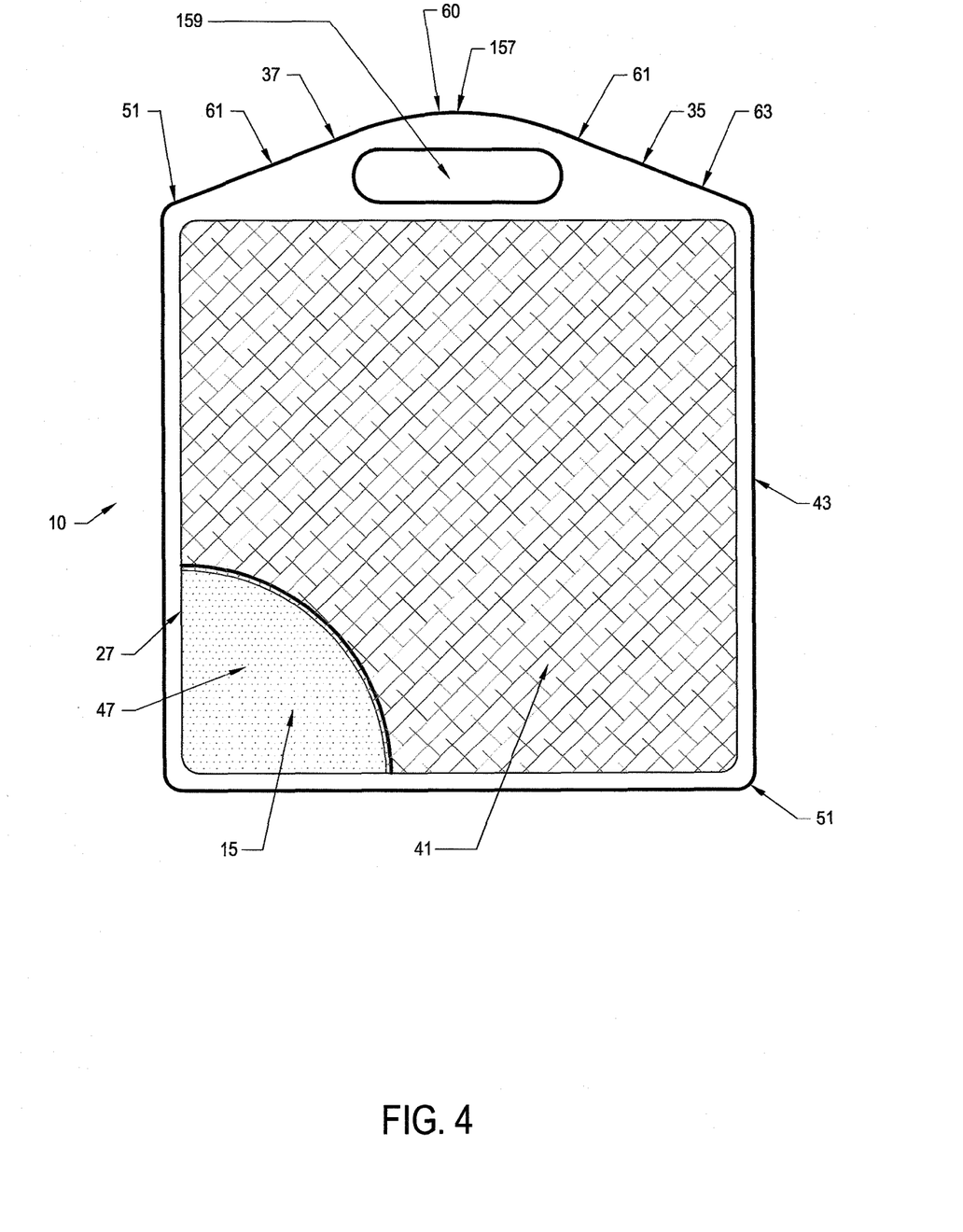
FIG. 4 is a front elevational view showing additional features of the invention.

FIG. 4 shows an alternative structure where the handle 157 extends across the entire width of the pad 10. The shape of the handle 157 is altered in that the handle has a wider shape and extends a smaller distance from the core of the pad. The aperture 159 in the handle is an elongated slot that is designed to accommodate several, preferably four, fingers of a user of the pad. The aperture 159 has a width from about to 2 about 7 inches and a height from about 0.5 of an inch to about 2 inches. The "four finger grip" on the well-known plastic shopping bas is to distribute weight from the bag to more fingers of the hand, making carrying easier. Conversely, the aperture 159 "four finger grip" of the present invention is designed to spread the load across the entire handle 157 and thus the entire pad 10. Further, since fingers generally share a common alignment, a four finger grip encourages the user to use more fingers, which tends to keep the handle reasonably straight, reducing distortion at the pad and eliminating the need for stiffening-ribs 53 in some versions of the pad 10. A heavy, liquid-laden pad has a natural propensity to distort which would be amplified if a single lifting point (such as a hold-tab or single finger handle) is utilized. This distortion not only increases the mechanical forces applied to the materials which could cause a rupture, the folding action also creates a "wringing" effect that would act to force the contents of the bag out through the one porous side, much like the way one wrings-out a wet rag or sponge. The other features of the pad are the same as previously described for the pad 10.

It is also possible that the fluid impervious sheet 35 can be made of a material upon which images can be printed. This would allow directions for use of the absorbent pad to be present on the fluid impervious sheet to assist in the proper utilization of the absorbent pad. In addition, product identification information could also be printed on the fluid impervious sheet.

Figure 3:
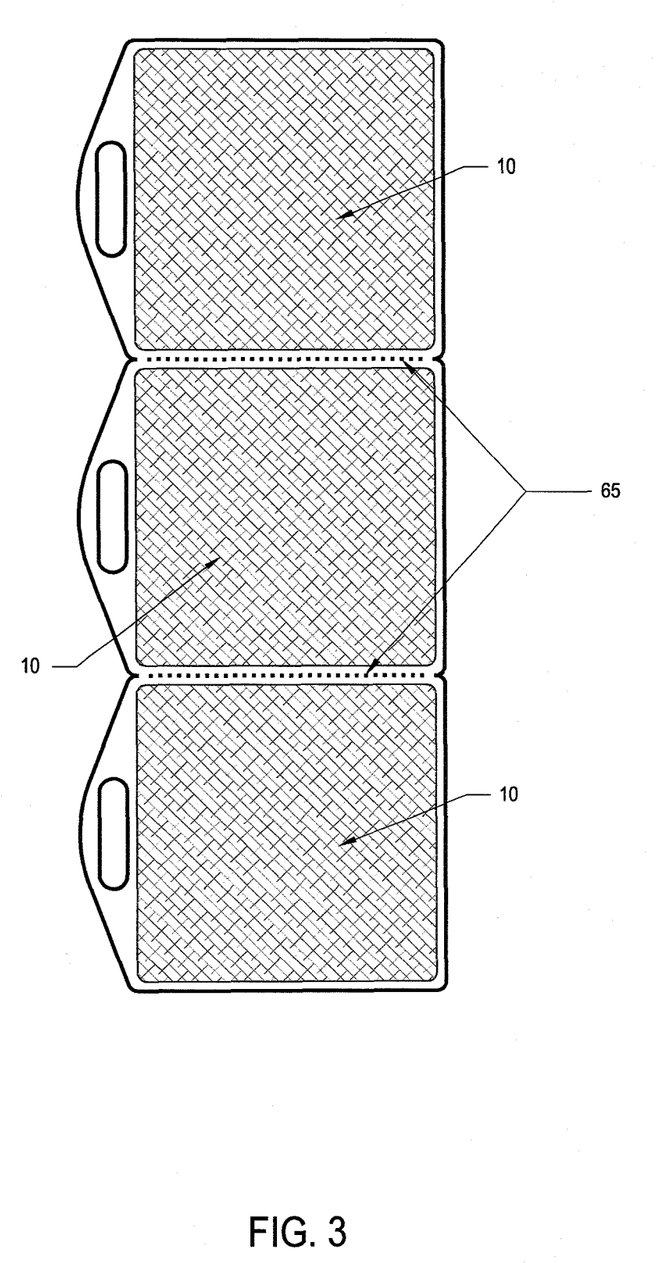
FIG. 3 is a front elevational view of an additional feature of the invention.

As shown in FIG. 3 a plurality of the absorbent pad 10 can be formed as part of a continuous sheet of pads. A plurality of perforations 65 are positioned between adjacent absorbent pads. This configuration would allow the absorbent pads to be sold in a continuous roll or package. An individual absorbent pad can be advanced and separated from the other absorbent pads in the package along the line of perforations 65. This would provide a very useful way for presenting the absorbent pads to potential users.

The absorbent pads of the present invention can be utilized in a multitude of applications to absorb and retain fluids. One of the anticipated uses would be to remove unwanted fluids, such as pet urine, from carpets. The use of the absorbent pad 10 will be described in relation to the removal of such a spot from a carpet, but it should be understood that other applications and uses can be made for the absorbent pad 10. When a spot, such as pet urine, is seen on a carpet, the absorbent pad 10 is positioned on the carpet with the non-woven sheet 41 disposed directly on the fluid that is to be removed. The handle 57, 157 can be gripped by the user and utilized to position the absorbent pad over the fluid. The non-woven sheet 41 wicks the fluid from the surface of the carpet and to the particles of super absorbent polymer 17 in the core 15. The super absorbent polymer absorbs and retains the fluid from the carpet. The user of the absorbent pad 10 can apply pressure to the fluid impervious sheet 35 that is spaced apart from the fluid to assist in moving or extracting the fluid from the carpet into contact with the super absorbent polymer where the fluid is absorbed and retained. The user of the absorbent pad 10 will be able to determine that fluid is being absorbed into the core 15 by observing the translucent fluid impervious sheet 35. The translucent nature of the fluid impervious sheet will, however, not allow the user to directly see the fluids that are being absorbed and retained. It has been determined, that in some applications, it is desirable to not have the user directly see the fluids that are being absorbed and retained. The translucent nature of the fluid impervious sheet 35 also allows the user to determine where the pad 10 is absorbing and retaining fluids. If the pad is not centered over the spill or spot the user will be aware of this and can reposition the pad to maximize the effectiveness of the pad.

Depending on the fluid and the quantity of fluid that is present on the carpet it may be necessary to leave the absorbent pad 10 in place for an extended period of time over the fluid that is to be removed from the carpet. The wicking characteristics of the non-woven layer 41 along with the absorption and retention characteristics of the super absorbent polymer in the core 15 will cause the pad 10 to continue to wick the fluid from the carpet until essentially all of the fluid that is to be removed has been absorbed and retained in the core 15. Professional carpet cleaners and most cleaning methods leave the carpet exposed to the air to final dry, causing many stains to reappear as the last vestiges of moisture evaporate from the top of the carpet fibers leaving the colorant nowhere to go. Leaving the pad 10 of the present invention in-place throughout the process, instead gives the colorant a disposable destination with improved results. Once the offending fluid has been removed, the absorbent pad 10 can be gripped by the handle 57, 157, removed from the carpet and disposed of. As the super absorbent polymer 17 in the core 15 functions to absorb and retain the fluid the offending fluid will not leak from the absorbent pad 10.

In some applications it may be desirable to add additional fluids to the fluids that are to be removed from the carpet. Water and other stain removal products can be added to the carpet where the spot is present. The water and other carpet cleaning fluids can be used to hydrate the spot on the carpet if the original fluids have dried or to provide additional hydration for the fluid that is to be removed. The additional fluids, such as water, provide a carrier for the original fluids that are to be removed from the carpet. The carriers assist in transporting the original fluid from the carpet to the non-woven sheet 41 where the combined fluids can be wicked to the super absorbent polymer of the core 15. The additional fluid also functions to carry the original fluid from recesses in the carpet and pad to allow a more complete removal of the original objectionable fluids from the carpet. In some applications it may be desirable to apply additional fluids, such as water, more than once to facilitate a complete as possible removal of the original offending fluids. Depending on the quantities of additional fluids utilized, it may be necessary to utilize more than one absorbent pad 10 to remove the additional fluids and the original objectionable fluid that soiled the carpet.

Figure 5:
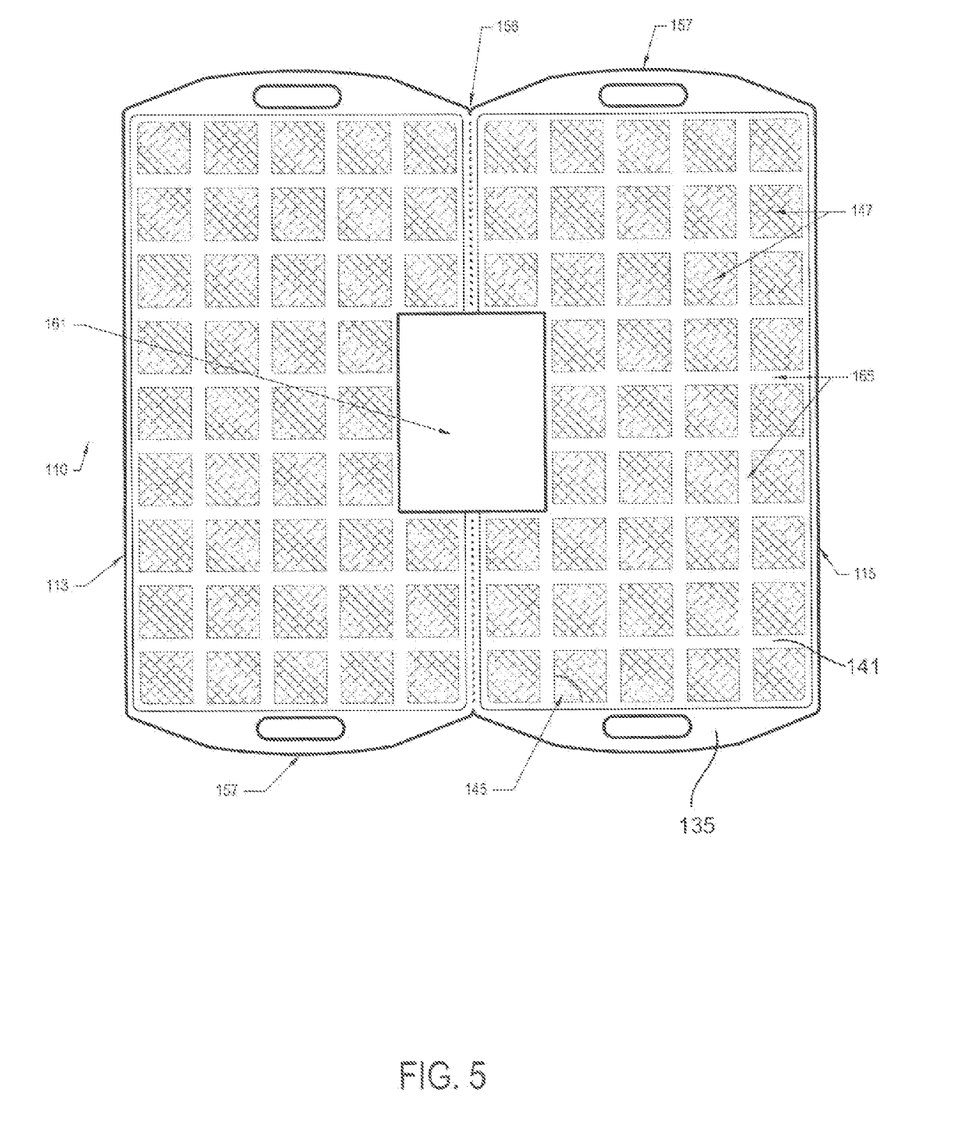
FIG. 5 is a front elevational view showing additional features of the invention.

FIG. 5 shows additional features that can be utilized with the pad of the present invention. The pad 110 is much larger then the previously described pads and is essentially two large pads joined together by a series of perforations 156. The perforations allow the first pad 113 to be removeably secured to the second pad 115 along the line of the series of perforations 156. The first pad 113 and the second pad 115 have a handle 157 located on opposite ends of the first and second pads. The handle is essentially the same configuration as previously shown and described with respect to FIG. 4. An opening 161 is provided in the pad 110 along the line of the series of perforations 156. The opening 161 is located essentially in the center of the pad 110. A plurality of enclosed spaces 147 are formed between the fluid impervious sheet 135 and the non-woven sheet 141. The core 145 is positioned in the plurality of enclosed spaces 147. The core is usually divided into a plurality of segments and a segment of the core is disposed in each of the plurality of enclosed spaces. The plurality of enclosed spaces 147 increase the strength of the pad 110 and different super absorbent polymer material can be positioned in the enclosed spaces 147. The super absorbent polymer material can vary in size, quantity and composition in the plurality of enclosed spaces. As an example, high fluid absorption rate polymer compositions could be positioned in the enclosed spaces 147 around the periphery of the pad 110 and high fluid absorption capacity super absorbent polymer could be positioned in the enclosed spaces 147 in the middle of the pad 110. Accordingly, it is possible to adjust the absorption characteristics of the pad 110 to achieve particular absorption characteristics for the pad. The borders 165 between plurality of enclosed spaces 147 provide an area where the pad can be cut to form a desired shape for the pad without compromising the integrity of the enclosed spaces.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

We claim:

1. An extraction and absorbent pad comprising:
   a core made of a super absorbent polymer laminate, the core having a first side and a second side;
   a fluid impervious sheet positioned on the first side of the core;
   a non-woven sheet positioned on the second side of the core, the non-woven sheet being designed to transfer fluids to the core, the fluid impervious sheet and the non-woven sheet being joined at the outer perimeter and forming an enclosed space for the core;
   a handle that is an extension of the fluid impervious sheet that extends beyond an outer peripheral boundary of the non-woven sheet for transporting the pad without touching the portion of the pad that absorbs fluids, the handle extends along substantially the entire width of a side of the pad.

2. The pad of claim 1 wherein the fluid impervious sheet is formed from a hydrophilic plastic.

3. The pad of claim 1 wherein the fluid impervious sheet is translucent to allow a user to determine that the pad has absorbed a fluid but not to see the fluid that has been absorbed.

4. The pad of claim 1 wherein the fluid impervious sheet and the non-woven sheet are bonded along the outer perimeter to form the enclosed space.

5. The pad of claim 1 wherein any corner formed by the joining of the fluid impervious sheet to the non-woven sheet are rounded to have enhanced strength to accommodate the large volume of fluid that can be absorbent and retained by the core.

6. The pad of claim 5 wherein the core has rounded edges that correspond to the rounded corners of the fluid impervious sheet and the non-woven sheet.

7. The pad of claim 1 wherein the handle extends along one side of the pad to spread out the load when lifting the pad and to keep the pad from folding when lifted by the handle.

8. The pad of claim 7 wherein an aperture is provided in the handle to assist in gripping the handle to lift or position the pad.

9. The pad of claim 8 wherein the aperture is a slot that is designed to accommodate more than one finger of the user.

10. The pad of claim 1 wherein the super absorbent polymer laminate contains particles of super absorbent polymer material.

11. The pad of claim 10 wherein the particle can vary in size and quantity in the laminate to vary the absorption and retention characteristics of areas of the pad.

12. The pad of claim 1 wherein the enclosed space can expand as fluid is absorbed and retained by the super absorbent polymer laminate.

13. The pad of claim 1 wherein an odor control substance is combined with the super absorbent polymer laminate.

14. The pad of claim 1 wherein a rib is formed in the handle to spread the load when lifting the pad and to keep the pad from folding.

15. The pad of claim 1 wherein more than one handle is provided on the pad.

16. The pad of claim 1 wherein a plurality of pads are joined together, a series of perforations being formed in the fluid impervious sheet and the non-woven sheet located between the pads to allow the plurality of pads to be separated.

17. An extraction and absorbent pad comprising:
a core made of a super absorbent polymer laminate, the core having a first side and a second side;
a fluid impervious sheet positioned on the first side of the core, more than one rib is formed in the fluid impervious sheet to keep the pad from folding;
a non-woven sheet positioned on the second side of the core, the non-woven sheet being designed to transfer fluids to the core, the fluid impervious sheet and the non-woven sheet being joined at the outer perimeter and forming an enclosed space for the core;
a handle attached to the fluid impervious sheet for transporting the pad without touching the portion of the pad that absorbs fluids.

18. An extraction and absorbent pad comprising:
a core made of a super absorbent polymer laminate, the core having a first side and a second side;
a fluid impervious sheet positioned on the first side of the core, more than one rib is formed in the fluid impervious sheet to keep the pad from folding;
a non-woven sheet positioned on the second side of the core, the non-woven sheet being designed to transfer fluids to the core, the fluid impervious sheet and the non-woven sheet being joined at the outer perimeter and forming an enclosed space for the core, the fluid impervious sheet and the non-woven sheet form a plurality of enclosed spaces and the core is positioned in each of the enclosed spaces;
a handle attached to the fluid impervious sheet for transporting the pad without touching the portion of the pad that absorbs fluids.

19. The pad of claim 18 wherein the core is divided into segments and a segment is positioned in each of the plurality of enclosed spaces.

20. The pad of claim 18 wherein the core of super absorbent polymer laminate contained in the plurality of enclosed spaces has particles of super absorbent polymer material, the particles can vary in size, quantity and composition in the plurality of enclosed spaces.

21. The pad of claim 20 wherein the fluid impervious sheet and the non-woven sheet form a boundary joint between the plurality of enclosed spaces.

22. The pad of claim 21 wherein an opening can be positioned in the pad to accommodate positioning the pad around a structure.

* * * * *